United States Patent [19]

Meng et al.

[11] Patent Number: 5,770,742

[45] Date of Patent: Jun. 23, 1998

[54] THIOPHENE-TRYPTAMINE DERIVATIVES

[75] Inventors: Qingchang Meng, Georgetown; Abdelmalik Slassi, Brampton; Sumanas Rakhit, Mississauga, all of Canada

[73] Assignee: Allelix Biopharmaceuticals Inc., Mississauga, Canada

[21] Appl. No.: 648,842

[22] Filed: May 16, 1996

[51] Int. Cl.⁶ .................................................. C07D 403/06
[52] U.S. Cl. ............................................................ 548/466
[58] Field of Search ............................................. 548/466

[56] References Cited

U.S. PATENT DOCUMENTS

| | | | |
|---|---|---|---|
| 5,317,103 | 5/1994 | Baker et al. | 544/367 |
| 5,510,362 | 4/1996 | Matassa et al. | 514/381 |
| 5,567,726 | 10/1996 | Baker et al. | 513/383 |

FOREIGN PATENT DOCUMENTS

| | | |
|---|---|---|
| WO 93/21178 | 10/1993 | WIPO . |
| WO 95/28400 | 10/1995 | WIPO . |
| WO 95/30655 | 11/1995 | WIPO . |
| WO 96/04274 | 2/1996 | WIPO . |

*Primary Examiner*—Jacqueline Haley
*Attorney, Agent, or Firm*—Ridout & Maybee

[57] ABSTRACT

5-Thiophene-substituted tryptamine analogs are provided, which exhibit selectivity towards $5\text{-HT}_{D1}$ receptors and consequently show potential in alleviation of the symptoms of migraine. The analogs are represented by the following general chemical formula:

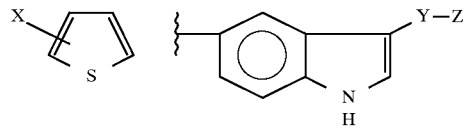

in which X represents H, $C_1$–$C_4$ alkyl, $C_1$–$C_4$ hydroxyalkyl or halogen, at the 4- or 5-position of the thiophene nucleus; Y represents a direct bond or a $C_1$–$C_3$ alkylene group optionally substituted with hydroxyl: and Z represents amino, mono- or di-N-lower alkyl-substituted amino, or optionally N-lower alkyl-substituted pyrrolidine.

23 Claims, No Drawings

THIOPHENE-TRYPTAMINE DERIVATIVES

FIELD OF THE INVENTION

This invention relates to novel chemical compounds active on the central nervous system (CNS). More particularly, it relates to novel tryptamine derivatives exhibiting selectivity towards certain human cell receptors, commonly known as serotonin or 5-HT receptors, and to compositions and uses of these novel compounds.

BACKGROUND OF THE INVENTION

Receptors are proteins disposed on the surface of cells. Serotonin, or 5-hydroxytryptamine, receptors are stimulated by serotonin (5-HT) and have been extensively studied. At least seven such 5-HT receptor types are known, denominated $5-HT_1$, $5-HT_2$ ... $5-HT_7$. 5-HT binds to different ones of these receptors in different ways, to give a signature profile.

The 5-HT receptor types can be further subdivided into subtypes; for example, receptor $5-HT_1$ has at least five subtypes denoted A, B, C, D and E. Within an individual subtype there may be further subdivisions. Thus $5-HT_{1D}$ subdivides to $5-HT_{1D\alpha}$ and $5-HT_{1D\beta}$.

It is desirable to find pharmaceutical compounds having a high degree of selectivity to a single receptor subtype, so that the drug will exhibit minimum side effects.

DESCRIPTION OF THE PRIOR ART

Sumatriptan, or 5-methylaminosulfonyltryptamine, of formula:

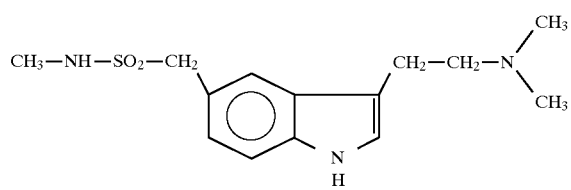

is an example of a pharmaceutical compound, currently on the market, which is a 5-HT receptor binder. It is prescribed for the treatment of migraine. It binds to the receptor $5-HT_{1F}$ and to the receptor $5-HT_{1D}$, with high affinity, to the substantial exclusion of other 5-HT receptors.

International Patent Publication WO 95/30655 Glennon discloses tryptamine analogs having an aminoethyl or (N-alkyl)aminoethyl substituent at position 3 of the indole nucleus and various arylalkyl, arylalkanoyl and arylalkanoyloxy groups at position 5 thereof. These are disclosed to be selective for binding to $5-HT_{1D}$ but nothing is said of their selectivity as between $5-HT_{1D\alpha}$ and $5-HT_{1D\beta}$.

International Patent Publication WO 93/21178 Pfizer discloses tryptamine analogs having a methyl pyrrolidine group substituted at position 3 of the indole nucleus, and a variety of optionally substituted phenyl or heterocyclic groups (pyridinyl, pyrimidinyl, pyridazinyl, pyrazinyl, furyl and thienyl) at position 5 of the indole nucleus. They are presented as compounds which are selective agonists at the $5-HT_1$ -like subtype of the 5-HT receptor. Example 64 shows the preparation of 5-(5-carbamoyl-2-thienyl)-3-(1-methylpyrrolidin-2(R)-ylmethyl)-1H-indole, and Example 67 reports some $5-HT_1$ receptor activity for it, but not its selectivity between various types of $5-HT_1$ receptors.

SUMMARY OF THE INVENTION

It is an object of the present invention to provide novel 5-substituted tryptamine derivatives.

It is a further object of the invention to provide such compounds which exhibit a high degree of binding selectivity as between the various $5-HT_{1D}$ receptor subtypes.

According to the present invention, there are provided novel 5-thiophene-substituted tryptamine analogs exhibiting selectivity towards $5-HT_{1D}$ receptors, and corresponding to general formula I:

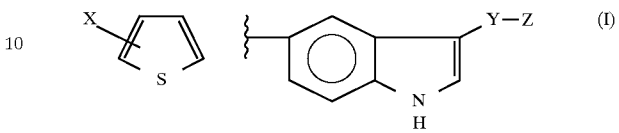

wherein X represents H, $C_1$–$C_4$ alkyl, $C_1$–$C_4$ hydroxyalkyl or halogen, at the 4- or 5-position of the thiophene nucleus, Y represents a direct bond or $C_1$–$C_3$ alkylene group optionally substituted with hydroxyl, and Z represents amino, mono- or di-N-lower alkyl-substituted amino, or optionally N-lower alkyl-substituted pyrrolidine.

Compounds of the present invention exhibit selective binding for the $5-HT_{1D}$ receptor, and in many cases exhibit selective binding for the $5-HT_{1D\alpha}$ receptor over the $5-HT_{1D\beta}$ receptor. Such selectivity renders them especially suitable for development as migraine treatment pharmaceutical compounds, with reduced side effects.

DESCRIPTION OF THE PREFERRED EMBODIMENTS

Preferred among the thiophene-tryptamine analog compounds of the present invention are those of the general formula (I) given above in which the thiophene group is unsubstituted, or substituted by a group selected from hydroxymethyl, methyl and chloro. When the thiophene ring is so substituted, the substituent is preferably at the 5-position of the thiophene ring, with the thiophene nucleus being bonded via its 2-position to the tryptamine nucleus.

When Z in the above general formula is chosen to be a pyrrolidine group, group Y is preferably a direct bond or methylene and the pyrrolidine group is bonded thereto either through the N-group of the cyclic structure or through any of the methylene groups thereof. In cases where the bond to Y is at a methylene group, the N-group of the pyrrolidine ring is preferably substituted with lower alkyl, preferably methyl. When Z in the above general formula is chosen to be amino or N-substituted amino, Y is preferably an ethylene group. The preferred N-substituent for the amino group is methyl.

Some of the compounds of the present invention have chiral centres, e.g. those in which Y is hydroxy-substituted alkylene and those in which Z is pyrrolidine bonded to Y via one of its methylene groups. The invention extends to cover all structural and optical isomers of the various compounds defined above, as well as racemic mixtures thereof.

Compounds of the present invention can be synthesized by processes generally known in the field of organic chemical synthesis. Thus, in general terms, an indole compound substituted at position 3 with the desired grouping—Y–Z, or an immediate precursor thereof, and substituted at position 5 with a leaving group such as halogen (chloride, bromide or iodide) or triflate ($OSO_2CF_3$) can be subjected to palladium-catalysed cross-coupling with a metallo-thiophene compound $R_1M$, wherein $R_1$ is an optionally substituted thiophene as previously described, and M is an optionally substituted metal substituent, at the 2- or 3-position of the thiophene ring, suitable for cross-coupling reactions. Examples of such M-groups are described in Synthesis 1991, pages 413 and 432 (and references quoted therein) and include (alkyl)$_3$Sn—, (alkyl)$_2$B—, (HO)$_2$B—, (alkoxy)$_2$B—, Li—, Cu—, chloroZn, haloMg—, arylHg— or chloroHg. The most preferred M group is (HO)$_2$B. The reaction takes place in an inert solvent, usually in the presence of a base, lithium chloride and a suitable catalyst. The choice of catalyst varies to some extent with the choice of group M and the structure of the substituted indole reactant. Suitable catalysts are palladium (II) and palladium (O) species such as palladium (II) acetate, palladium (II) chloride, bis(triphenylphosphine) palladium (II) chloride and tetrakis(triphenylphosphine)palladium (O). The preferred catalyst is tetrakis(triphenylphosphine)palladium (O). Suitable bases include tertiary amines, sodium bicarbonate and sodium carbonate, with sodium carbonate being preferred. Suitable inert solvents include acetonitrile, N,N-dimethylformamide and 1,2-dimethoxyethane, with 1,2-dimethoxyethane being preferred. The reaction suitably takes place at a temperature of from 25°–100° C., preferably 50°–100° C. Compounds R$_1$M can be prepared from compounds R$_1$T where T represents halo or triflate by metallation reaction under suitable conditions. For example, a compound R$_1$M where M is B(OH)$_2$ can be prepared by treating R$_1$Br with n-butyl lithium in tetrahydrofuran at −78° C. followed by addition of a trialkylborate such as trimethylborate, followed by a work-up with 1M aqueous hydrochloric acid.

In some instances the desired grouping at the 5-position of the indole is best attached in the reverse fashion, where the metal substituent is on the indole and the leaving group on the thiophene, under the same palladium-catalysed conditions described above. The 5-metal-substituted indole can be prepared by reacting an indole compound substituted at the 3-position with the desired grouping, Y–Z, or an immediate precursor thereof, and substituted at the 5-position with an appropriate leaving group, under metallation conditions, e.g. bis(tributyltin) in the presence of palladium catalyst in 1,2-dimethoxyethane. The appropriately substituted thiophenes with a leaving group in the 2- or 3-position are commercially available or can be prepared using standard methods known to one skilled in the art.

The 3-substituted indole precursor compounds for the cross-coupling with compound R$_1$—M can be prepared by different methods known in organic chemical synthesis, depending on the choice of the 3-substituent, i.e. the grouping —Y–Z for the compounds of the present invention. When Y is a direct bond and Z is 1-substituted 3-pyrrolidinyl, the precursor compound, of formula:

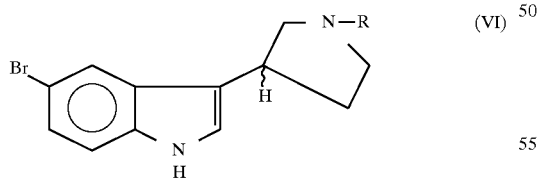

(VI)

can be prepared according to the following general scheme:

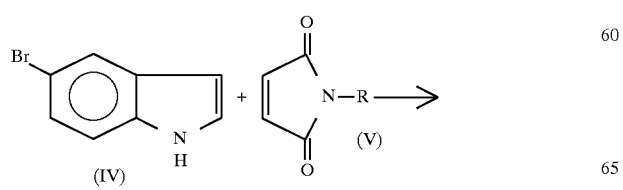

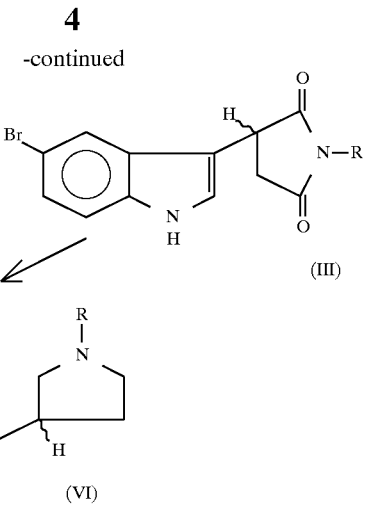

The 5-substituted indole compound IV and the 1-substituted maleimide compound V are compounds known in the art. They can be condensed together to form the compound of formula III by reaction in an inert solvent at a temperature of from about 65° C. to about 154° C., preferably from about 100° C. to about 110° C. Suitable solvents include C$_1$–C$_3$ alcohols, acetic acid, formic acid and N,N'-dimethylformamide, with acetic acid being preferred. Compounds of formula III can be converted to compounds of formula VI by reduction, e.g. using lithium aluminum hydride, lithium borohydride or diborane as reducing agent, in an inert solvent such as tetrahydrofuran, dioxane, diethyl ether or other ethers, at temperatures from about 25° C. to 100° C. Preferred is reduction with lithium aluminum hydride in tetrahydrofuran at a temperature of about 65° C.

For the preparation of compounds according to the invention in which Y represents a methylene group and Z represents 1-substituted-2-pyrrolidinyl, the precursor compound for reaction with R$_1$M as defined above is, for example, of formula XIII:

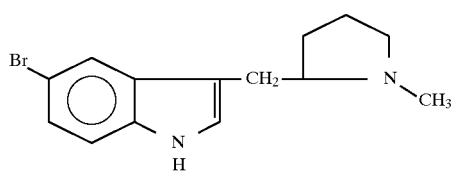

and can be prepared as follows:

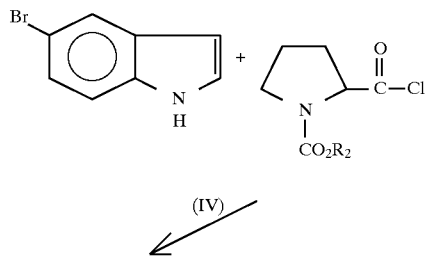

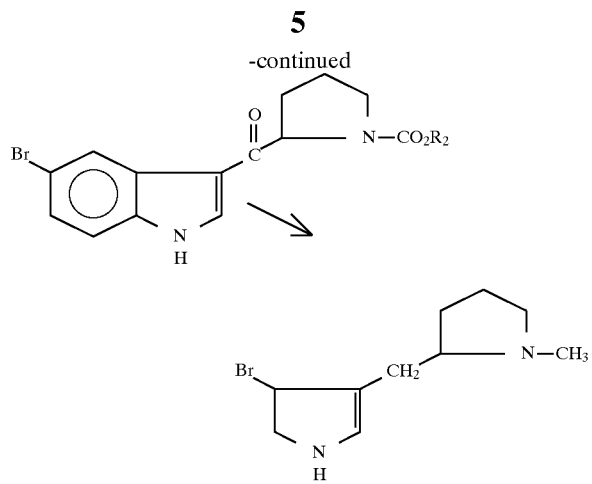

Compound XII in which $R_2$ is for example benzyl or t-butyl, can be condensed with the substituted indole compound IV typically by first converting the 5-haloindole IV to a magnesium derivative by reaction with a suitable Grignard reagent, such as t-butyl- or ethyl-magnesium bromide, in an inert solvent. Then the magnesium derivative so formed can be reacted in situ with the reagent of formula XII. Suitable inert solvents include tetrahydrofuran and diethylether (which is preferred). The reaction can be conducted at temperatures ranging from −30° to 65° C., suitably at room temperature. Compound XIII is prepared from compound XI by reduction using a reducing agent such as lithium aluminum hydride in solution in an inert solvent such as dioxane, diethyl ether, similar other ethers or, preferably, tetrahydrofuran. The free 2- carboxylic acid version of compound XII is known. The acyl chloride thereof is prepared by reaction of the free acid with oxalyl chloride and a trace amount of N,N-dimethylformamide in dichloromethane at temperatures ranging from −10° to 25° C.

Preparation of compounds according to the present invention but in which Y in formula I is alkylene and Z in formula I is amino, alkylamino or 1-N-pyrrolidine can be prepared from a precursor of formula XV:

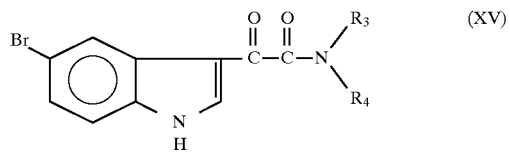

by reaction with $R_1M$ under palladium-catalysed cross-coupling conditions as previously described, followed by reduction of the side chain carbonyl groups to methylene groups. This reduction can be carried out in solution in an inert solvent (dioxane, diethyl ether, other similar ethers or, preferably, tetrahydrofuran) using as reducing agent lithium borohydride, diborane or, preferably, lithium aluminum hydride, and at temperatures within the approximate range 25°–100° C., preferably about 90° C. Compounds of formula XV can be prepared by reaction of the 5-substituted indole (IV) with oxalyl chloride followed by reaction with the appropriate amine, thus:

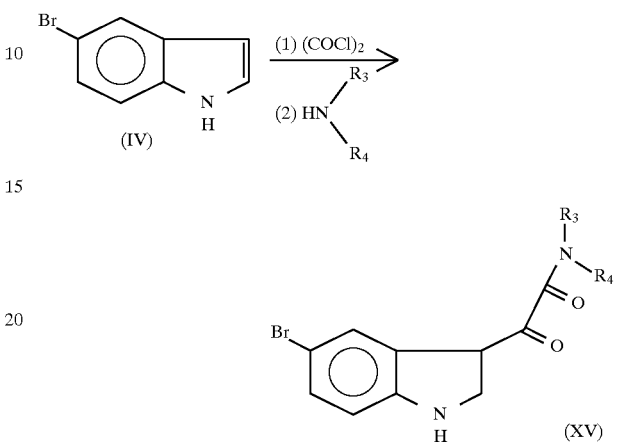

in which $R_3$ and $R_4$ are H, lower alkyl or alkylene joined to N to form the pyrrolidine ring. These reactions are conducted in an inert solvent such as diethyl ether (preferred) or dichloromethane, and at temperatures in the range 0°–65° C., preferably 25°–65° C.

An alternate synthesis method for compounds according to the invention in which Y is alkylene and Z is amino utilizes as starting materials serotonin and an N-carboalkoxyphthalimide, which can be reacted together in aqueous solution in the presence of a base to form 5-hydroxy-3-(2-phthalimidoalkyl)-1H-indole. This compound can then be reacted with trifluoromethane sulfonic anhydride to replace the 5-hydroxy group with a triflate leaving group. The resulting compound, appropriately protected at position 1, can be subjected to palladium-catalyzed cross-coupling with a metallo-thiophene as previously described, followed by deprotection, to produce a compound according to the invention in satisfactory yield. Specifically preferred chemical compounds according to the present invention with their specific substituent groups related to compound I above, are listed below in Table 1.

TABLE 1

| No. | Group X | Thiophene Bond Position | Group Y | Group Z | Corresponding Example # | Stereo-chemistry |
|---|---|---|---|---|---|---|
| 1 | H | 2 | −CH$_2$− | ⟨N−CH$_3$ pyrrolidine⟩ | 8b | R |

TABLE 1-continued

| No. | Group X | Thiophene Bond Position | Group Y | Group Z | Corresponding Example # | Stereo-chemistry |
|---|---|---|---|---|---|---|
| 2 | H | 3 | —CH$_2$— | pyrrolidin-2-yl N—CH$_3$ | 8a | R |
| 3 | H | 3 | —CH$_2$—CH$_2$— | —N(CH$_3$)$_2$ | 2c | — |
| 4 | H | 2 | —CH$_2$—CH$_2$ | —N(CH$_3$)$_2$ | 2b | — |
| 5 | 5-(HO—CH$_2$)— | 2 | —CH$_2$—CH$_2$— | —N(CH$_3$)$_2$ | 4b | — |
| 6 | H | 2 | —CH$_2$— | pyrrolidin-2-yl N—CH$_3$ | 8c | S |
| 7 | H | 2 | —CH$_2$—CH$_2$ | —NH$_2$ | 12 | — |
| 8 | H | 2 |  | pyrrolidin-3-yl N—CH$_3$ | 7a | racemic |
| 9 | 5-Cl | 2 | —CH$_2$—CH$_2$— | —N(CH$_3$)$_2$ | 2d | — |
| 10 | H | 3 | CH(OH)—CH$_2$— | —N(CH$_3$)$_2$ | 2e | racemic |
| 11 | H | 2 | —CH$_2$—CH$_2$— | —N(pyrrolidinyl) | 2a | — |
| 12 | 5-CH$_3$ | 2 | —CH$_2$—CH$_2$— | —N(CH$_3$)$_2$ | 4a | — |
| 13 | H | 3 |  | pyrrolidin-3-yl N—CH$_3$ | 7b | racemic |

In an embodiment of the invention, the compound is provided in labelled form, such as radiolabelled form e.g. labelled by incorporation within its structure $^3$H or $^{14}$C or by conjugation to $^{125}$I. In another aspect of the invention, the compounds in labelled form can be used to identify 5-HT$_{1D}$ receptor ligands by techniques common in the art. This can be achieved by incubating the receptor in the presence of a ligand candidate and then incubating the resulting preparation with an equimolar amount of radiolabelled compound of the invention. 5-HT$_{1D}$ ligands are thus revealed as those that are not significantly displaced by the radiolabelled compound of the present invention. Alternatively, 5-HT$_{1D}$ ligand candidates may be identified by first incubating a radiolabelled form of a compound of the invention then incubating the resulting preparation in the presence of the candidate ligand. A more potent 5-HT$_{1D}$ ligand will, at equimolar concentration, displace the radiolabelled compound of the invention.

The serotonin-like binding affinity of the compounds indicates their utility as pharmaceuticals useful for the treatment of various conditions in which the use of a 5-HT$_{1D}$ ligand is indicated, such as for the treatment of migraine, cluster headache and portal tension, a condition characterized by increased portal vein blood flow and typically associated with cirrhosis of the liver.

For use in medicine, the compounds of the present invention are administered as standard pharmaceutical compositions. The present invention therefore provides in a further aspect pharmaceutical compositions comprising a compound of formula (I) or a pharmaceutically acceptable salt, solvate or hydrate thereof and a pharmaceutically acceptable carrier. Compounds of the present invention may be administered by any convenient route, for example by oral, parenteral, buccal, sublingual, nasal, rectal or transdermal administration and the pharmaceutical compositions adapted accordingly.

The compounds and their pharmaceutically acceptable salts which are active when given orally can be formulated as liquids, for example syrups, suspensions or emulsions; tablets, capsules and lozenges. Liquid formulations will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. Compositions in the form of tablets can be prepared using any suitable pharmaceutical carrier routinely used for preparing solid formulations. Examples include magnesium stearate, starch, lactose, sucrose and cellulose. Compositions in the form of capsules can be prepared using routine encapsulation procedures. For example, pellets containing active ingredient can be prepared using standard carriers and then filled into hard gelatin capsules; alternatively, a dispersion or suspension can be prepared using a suitable pharmaceutical carrier, for example aqueous gums, celluloses, silicates or oils and the dispersion or suspension filled into soft gelatin capsules.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration. Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Each dosage unit for oral administration contains preferably from 1 to 250 mg (and for parenteral administration contains preferably from 01. to 25 mg) of a compound of the formula (I) or a pharmaceutically acceptable salt thereof calculated as the free base. The pharmaceutically acceptable compounds of the invention will normally be administered in a daily dosage regimen (for an adult patient) of, for example, an oral dose of from 1 mg to 500 mg, preferably between 10 mg and 400 mg, e.g. between 10 mg and 250 mg, or an intravenous, subcutaneous, or intramuscular dose of between 0.1 mg and 100 mg, preferably between 0.1 mg and 50 mg, e.g., between 1 mg and 25 mg, of the compound of formula (I) or a pharmaceutically acceptable salt, solvate or hydrate thereof calculated as the free base, the compound being administered 1 to 4 times per day. Suitably, the compounds will be administered for a period of continuous therapy, for example for a week or more.

Specific description of the Most Preferred Embodiments

EXAMPLE 1(a)

5-Bromo-3-(pyrrolidinylglyoxyl)-1H-indole

To a solution of 5-bromoindole (3.92 g, 20 mmol) in ether (50 mL), cooled to 0° C., was added a solution of oxalyl chloride in dichloromethane (2M, 10 mL) dropwise. The resulting mixture was stirred at room temperature overnight and then cooled to 0° C. and pyrrolidine (6.7 mL, 80 mmol) was added dropwise. After stirring for 2 hours at room temperature, the mixture was poured into water (50 mL) and extracted with dichloromethane (3×100 mL). The combined organic phases were dried over sodium sulfate and evaporated to a white amorphous solid which was washed with ethyl acetate (50 mL) to give the title compound (2.87 g, 45%). m.p. 212°–213° C.; $^1$H NMR (CDCl$_3$, 300 MHz) δ: 10.69 (s, 1H), 8.49 (d, J=1.5 Hz, 1H), 7.87 (d, J=3.0 Hz, 1H), 7.31 (dd, J=8.6, 1.5 Hz, 1H), 7.17 (d, J=8.6 Hz, 1H), 3.59 (m, 4H), 1.94 (m, 4H).

In a like manner the following additional compound was prepared:
(b) 5-Bromo-3-(N,N-dimethylaminoglyoxyl)-1H-indole, from N,N-dimethylamine; $^1$H NMR (CDCl$_3$, 300 MHz) δ: 10.05 (s, 1H), 8.48 (d, J=1.5 Hz, 1H), 7.71 (d, J=2.4 Hz, 1H), 7.35 (dd, J=1.5, 8.5 Hz, 1H), 7.19 (d, J=8.5 Hz, 1H), 3.10 (s, 3H), 3.06 (s, 3H).

EXAMPLE 2(A)

3-(2-Pyrrolidinylethyl)-5-(2-thienyl)-1H-indole

To a solution of 5-bromo-3-(pyrrolidinylglyoxyl)-1H-indole (Example 1a) (0.642 g, 2 mmol) in 1,2-dimethoxyethane (50 mL) was added tetrakis (triphenylphosphine)palladium (0.465 g, 0.4 mmol) and the resulting mixture was stirred under argon at room temperature for 20 minutes. Thiophene-2-boronic acid (0.384 g, 3 mmol) and sodium carbonate (2M solution in water, 2 mL) were then added. The mixture was stirred at reflux under argon for 6 hours, cooled to room temperature and poured onto a silica gel column. Elution with hexane/ethyl acetate (1:1) followed by ethyl acetate provided 3-(2-pyrrolidinylglyoxyl)-5-(2-thienyl)-1H-indole as a crude yellow solid (0.640 g) which was used directly for the next reaction. 3-(2-Pyrrolidinylglyoxyl)-5-(2-thienyl)-1H-indole was dissolved in tetrahydrofuran (100 mL) and cooled to 0° C. To this solution was added lithium aluminum hydride (1M solution in tetrahydrofuran, 16.5 mL) dropwise and the resulting mixture was stirred at reflux for 4 hours, cooled to 0° C., quenched with saturated ammonium chloride solution (4 mL), filtered through celite and thoroughly rinsed with ethyl acetate. The filtrate was poured onto a silica gel column and eluted with methanol/ammonium hydroxide (50:1) to provide the title compound as a colorless syrup (0.160 g, 27% for two steps). HRMS (FAB): MH$^+$ for C$_{18}$H$_{20}$N$_2$S, calculated 297.14255, found 297.14164.

In a like manner the following additional compounds were prepared:
(b) 3-(2-N,N-Dimethylaminoethyl)-5-(2-thienyl)-1H-indole, from 5-bromo-3-(N,N-dimethylaminoglyoxyl)-1H-indole (Example 1b). Syrup; HRMS (FAB): MH$^+$ for C$_{16}$H$_{18}$N$_2$S, calculated 271.12689, found 271.12707.
(c) 3-(2-N,N-Dimethylaminoethyl)-5-(3-thienyl)-1H-indole, from 5-bromo-3-(N,N-dimethylaminoglyoxyl)-1H-indole (Example 1b) and thiophene-3-boronic acid. Syrup; $^1$H NMR (CDCl$_3$, 300 MHz) δ: 8.15 (s, 1H), 7.81 (s, 1H), 7.46–7.35 (m, 5H), 7.04 (s, 1H), 3.02 (m, 2H), 2.72 (m, 2H), 2.40 (s, 6H).
(d) 5-(5-Chlorothien-2-yl)-3-(2-N,N-dimethylaminoethyl)-1H-indole, from 5-bromo-3-(N,N-dimethylaminoglyoxyl)-1H-indole (Example 1b) and 5-chlorothiophene-2-boronic acid. Syrup; HRMS (FAB): MH$^+$ for C$_{16}$H$_{17}$ClN$_2$S, calculated 305.08792, found 305.08705.
(e) (±)-3-(2-N,N-Dimethylamino-1-hydroxylethyl)-5-(3-thienyl)-1H-indole, from Example 2c as a side product. Syrup; HRMS (FAB): MH$^+$ for C$_{16}$H$_{18}$N$_2$OS, calculated 287.12180, found 287.12176.

EXAMPLE 3

3-(N,N-Dimethylaminoglyoxyl)-5-tributylstannyl-1H-indole

To a solution of 5-bromo-3-(N,N-dimethylaminoglyoxyl)-1H-indole (Example 1b) (1.2 g, 4.1 mmol) in 1,2-dimethoxyethane (40 mL) was added tetrakis (triphenylphosphine)palladium (0.950 g, 0.82 mmol) and the resulting mixture was stirred at room temperature for 20 minutes under argon. Bis(tributyltin) (2.5 mL, 4.9 mmol) was then added and the mixture stirred at reflux for 6 hours. After cooling to room temperature, the mixture was filtered through celite and thoroughly rinsed with ethyl acetate. The filtrate was washed with water (200 mL), dried over sodium sulfate and evaporated to dryness. Silica gel chromatography using hexane/ethyl acetate (1:1) and then ethyl acetate as eluent provided the title compound as a yellow syrup (0.876 g, 42%).

EXAMPLE 4(a)

3-(2-N,N-Dimethylaminoethyl)-5-(5-methylthien-2-yl)-1H-indole 3-(N,N-Dimethylaminoglyoxyl)-5-tributylstannyl-1H-indole (Example 3) (0.388 g, 0.77 mmol), 5-bromo-2-thiophenecarboxaldehyde (0.176 g, 0.92 mmol) and tetrakis (triphenylphosphine) palladium (0.089 g, 0.077 mmol) were mixed in N,N-dimethylformamide (20 mL) and stirred at 100° C. under argon for 24 hours. After cooling to room temperature, the mixture was poured into water (30 mL) and extracted with diethyl ether (3×30 mL). The organic phase was dried over sodium sulfate and evaporated to dryness. Silica gel chromatography using ethyl acetate as eluent gave crude 3-(2-N,N-dimethylaminoglyoxyl)-5-(5-formylthien-2-yl)-1H-indole as a syrup which was used directly for the next reaction.

3-(2-N,N-Dimethylaminoglyoxyl)-5-(5-formylthien-2-yl)-1H-indole was dissolved in tetrahydrofuran (20 mL) and a solution of lithium aluminum hydride (1M in tetrahydrofuran, 7.7 mL) was slowly added. The resulting mixture was stirred at reflux for 4 hours, then cooled to 0° C., quenched with saturated ammonium chloride (3 mL) and filtered through celite with thorough rinsing with ethyl acetate. The filtrate was poured onto a silica gel column and eluted with methanol and methanol/ammonium hydroxide (98:2) to provide a mixture of 2 products. Further chromatographic purification on alumina (basic activity I) using dichloromethane/methanol/ammonium hydroxide (250:7:1) as eluent provided the title compound as a syrup (12 mg, 5% for 2 steps). HRMS (FAB): MH$^+$ for $C_{17}H_{20}N_2S$, calculated 285.14255, found 285.14332.
(b) 3-(2-N,N-Dimethylaminoethyl)-5-(5-hydroxymethylthienyl-2-yl)-1H-indole, from Example 4a as a side product (6 mg, 3% for 2 steps). Syrup; HRMS (FAB): MH$^+$ for $C_{17}H_{20}N_2OS$, calculated 301.13745, found 301.13350.

EXAMPLE 5

5-Bromo-3-(N-methylpyrrolidin-3-yl)-1H-indole

To a solution of 5-bromoindole (5 g, 25.50 mmol) in glacial acetic acid (60 mL) was added N-methylmaleimide (6.1 g, 56.11 mmol) and the resulting mixture was heated to reflux for 4 days. The excess acetic acid was distilled and the crude product dissolved in diethyl ether (500 mL) and washed with saturated sodium bicarbonate (2×100 mL) and brine (3×100 mL). The solvent was evaporated and the residue chromatographed on silica gel using hexane/ethyl acetate (1:1) as the eluent to provide 3-(5-bromo-1H-indol-3-yl)-N-methylsuccinimide (5.85 g, 75%) which was used directly for the next reaction. Yellow solid, m.p. 194°–195° C.

To a stirred solution of 3-(5-bromo-1H-indol-3-yl)-N-methylsuccinimide (1.3 g, 4.23 mmol) in anhydrous tetrahydrofuran (12 mL) at 0° C., was added lithium aluminum hydride (1M solution in tetrahydrofuran, 9.3 mL, 9.3 mmol). The resulting mixture was heated to reflux under argon for 2 hours, then cooled to 0° C. and quenched with cold water (2 mL) and ammonium hydroxide (15 mL). The resulting solution was stirred at room temperature for 1 hour and then filtered through celite. The filtrate was evaporated to dryness and the crude product extracted into ethyl acetate (250 mL). The solvent was once again evaporated and the product purified by silica gel chromatography using chloroform/ammonia(2M in methanol) (9:1) as the eluent to provide the title compound as a white solid (0.700 g, 64%). m.p. 152°–154° C.; HRMS (FAB): MH$^+$ for $C_{13}H_{15}{}^{79}BrN_2$, calculated 279.0496, found 279.0478.

EXAMPLE 6(a)

3-(N-Benzyloxycarbonylpyrrolidin-2R-ylcarbonyl)-5-bromo-1H-indole

To a stirred solution of N-benzyloxycarbonyl-R-proline (2.5 g, 10.03 mmol) in anhydrous methylene chloride was added a solution of oxalyl chloride (2M solution in methylene chloride, 7 mL, 15.04 mmol). The resulting mixture was stirred at room temperature under argon for 2 hours. The solvent and excess oxalyl chloride was evaporated under reduced pressure and the crude product washed with hexane (3×10 mL) and evaporated to dryness to provide N-benzyloxycarbonyl-R-proline acid chloride which was used directly for the next reaction. N-Benzyloxycarbonyl-R-proline acid chloride from the above reaction was dissolved in anhydrous diethyl ether (30 mL) and added at 0° C. to a solution of 5-bromoindole (2.9 g, 15.04 mmol) and t-butylmagnesium chloride (2M solution in diethyl ether, 8.3 mL, 16.549 mmol) in anhydrous diethyl ether (30 mL). The resulting mixture was stirred at room temperature under argon for 45 minutes and then ethyl acetate (150 mL) and saturated sodium bicarbonate (30 mL) were added. The organic layer was dried and evaporated under reduced pressure to provide a yellow oil. The title compound was crystallized using hexane/ethyl acetate (9:1) to provide a white solid (3.07 g, 72%). m.p. 95°–96° C.

In a like manner the following additional compound was prepared:
(b) 3-(N-Benzyloxycarbonylpyrrolidin-2S-ylcarbonyl)-5-bromo-1H-indole, from N-benzyloxycarbonyl-S-proline; m.p. 95°–96° C.

EXAMPLE 7(a)

3-(N-Methylpyrrolidin-3-yl)-5-(2-thienyl)-1H-indole

To a stirred solution of 5-bromo-3-(N-methylpyrrolidin-3-yl)-1H-indole (Example 5) (0.420 g, 1.50 mmol) in ethylene glycol dimethyl ether (12 mL) was added a catalytic amount of tetrakis(triphenylphosphine)palladium and the resulting mixture was stirred at room temperature for 15 minutes. Thiophene-2-boronic acid (0.215 g, 1.68 mmol) was then added followed by sodium bicarbonate (0.478 g, 4.52 mmol) in water (3 mL) and the resulting mixture was refluxed with vigorous stirring under argon overnight. The organic solvent was evaporated under reduced pressure and the crude product was extracted into ethyl acetate (3×100 mL). After drying and evaporating, the product was purified by silica gel chromatography to provide a yellow solid (0.311 g, 73%). m.p. 85°–86° C.; HRMS (FAB): MH$^+$ for $C_{17}H_{18}N_2S$, calculated 283.12689, found 283.12680.

In a like manner the following additional compounds were prepared:
(b) 3-(N-Methylpyrrolidin-3-yl)-5-(3-thienyl)-1H-indole, from thiophene-3-boronic acid. White solid, 78% yield; m.p. 60°–62° C.
(c) 3-(N-Benzyloxycarbonylpyrrolidin-2S-ylcarbonyl)-5-(2-thienyl)-1H-indole, from 3-(N-benzyloxycarbonylpyrrolidin-2S-ylcarbonyl)-5-bromo-1H-indole (Example 6b).

(d) 3-(N-Benzyloxycarbonylpyrrolidin-2R-ylcarbonyl)-5-(2-thienyl)-1H-indole, from 3-(N-benzyloxycarbonylpyrrolidin-2R-ylcarbonyl)-5-bromo-1H-indole (Example 6a). m.p. 178°–180° C.
(e) 3-(N-Benzyloxycarbonylpyrrolidin-2R-ylcarbonyl)-5-(3-thienyl)-1H-indole, from 3-(N-benzyloxycarbonylpyrrolidin-2R-ylcarbonyl)-5-bromo-1H-indole (Example 6a) and thiophene-3-boronic acid. m.p. 166°–168° C.

EXAMPLE 8(a)

3-(N-Methylpyrrolidin-2R-ylmethyl)-5-(3-thienyl)-1H-indole

To a stirred solution of 3-(N-benzyloxycarbonylpyrrolidin-2R-ylcarbonyl)-5-(3-thienyl)-1H-indole (Example 7e) (0.400 g, 0.726 mmol) in anhydrous tetrahydrofuran (7 mL) at 0° C. was added a solution of lithium aluminum hydride (1M solution in tetrahydrofuran, 4.3 mL, 4.3 mmol). The resulting mixture was stirred at room temperature under argon for 30 minutes and then heated to reflux for 4 hours. The reaction mixture was then cooled to 0° C. and quenched with water (1 mL) and ammonium hydroxide (5 mL) and then stirred at room temperature for 1 hour. The mixture was filtered through celite, evaporated and extracted into chloroform (150 mL). Purification by silica gel chromatography using chloroform/ammonia (2M in methanol) (9:1) as the eluent provided the title compound as a yellow oil (0.133 g, 62%).

In a like manner the following additional compounds were prepared:
(b) 3-(N-Methylpyrrolidin-2R-ylmethyl)-5-(2-thienyl)-1H-indole, from 3-(N-benzyloxycarbonylpyrrolidin-2R-ylcarbonyl)-5-(2-thienyl)-1H-indole (Example 7d). White solid, 49% yield; m.p. 48°–50° C.; HRMS (FAB): MH$^+$ for $C_{18}H_{20}N_2S$ calculated 297.14255, found 297.14085.
(c) 3-(N-Methylpyrrolidin-2S-ylmethyl)-5-(2-thienyl)-1H-indole, from 3-(N-benzyloxycarbonylpyrrolidin-2S-ylcarbonyl)-5-(2-thienyl)-1H-indole (Example 7c). Off-white solid, 42% yield; HRMS (FAB): MH$^+$ for $C_{18}H_{20}N_2S$, calculated 297.14255, found 297.14301.

EXAMPLE 9

5-Hydroxy-3-(2-phthalimidoethyl)-1H-indole

To a suspension of serotonin creatinine sulfate monohydrate (5 g, 12.333 mmol) in water (80 mL) were added N-carbethoxyphthalimide (2.84 g, 1.30 mmol) and potassium carbonate (3.54 g, 24.6 mmol). The resulting mixture was stirred at room temperature for 4 hours. The precipitate was filtered, washed with water and dried to give the title compound (3.8 g, 100%) as a yellow solid. $^1$H NMR (CD$_3$SOCD$_3$, 300 MHz) δ: 10.52 (s, 1H), 8.64 (s, 1H), 7.87–7.83 (A2B2 system, 4H), 7.12 (d, J=8.6 Hz, 1H), 7.08 (broad s, 1H), 6.89 (broad s, 1H), 6.60 (broad d, J=8.6 Hz, 1H).

EXAMPLE 10

3-(2-Phthalimidoethyl)-5-trifluoromethanesulfonyloxy-1H-indole

To a solution of 5-hydroxy-3-(2-phthalimidoethyl)-1H-indole (Example 9) (1.23 g, 4 mmol) in acetonitrile (15 mL) were added trifluoromethanesulfonic anhydride (1.5 mL, 8.8 mmol) and triethylamine (2.5 mL, 17.6 mmol) at 0° C. and the resulting mixture was stirred for 2 hours at room temperature under argon. Methanol (0.5 mL) was then added and the mixture stirred for 10 minutes and then poured into ethyl acetate (50 mL), washed with water (2×50 mL), dried over magnesium sulfate and evaporated under reduced pressure. The residue was passed through a short silica gel column using hexane/ethyl acetate (2:1) as the eluent. Crystallization from hexane/ethyl acetate gave the title compound as white needles. $^1$H NMR (CD$_3$COCD$_3$, 300 MHz) δ: 10.45 (s, 1H), 7.81–7.71 (A2B2 system, 4H), 7.53 (d, J=8.9 Hz, 1H), 7.40 (d, J=2.1 Hz, 1H), 7.13 (dd, J=2.1 and 8.9 Hz, 1H), 3.96 (t, J=7.3 Hz, 2H), 3.17 (t, J=7.3 Hz, 2H); $^{13}$C NMR (CD$_3$COCD$_3$, 300 MHz) δ: 168.6, 144.2, 136.4, 134.8, 132.9, 128.6, 126.6, 123.6, 119.7 (CF$_3$), 115.2, 113.50, 113.46, 111.6, 38.9, 24.6.

EXAMPLE 11

3-(2-Phthalimidoethyl)-1-(p-toluenesulfonyl)-5-(trifluoromethanesulfonyl-oxy)-1H-indole To a solution of 3-(2-phthalimidoethyl)-5-trifluoromethanesulfonyloxy-1H-indole (Example 10) (0.640 g, 1.46 mmol) in anhydrous acetonitrile (15 mL) was added sodium hydride (60% dispersion in mineral oil, 0.335 g, 23.3 mmol) and the resulting mixture was stirred at room temperature under argon for 5 minutes. p-Toluenesulfonyl chloride (0.333 g, 1.75 mmol) was then added and the mixture stirred at room temperature for 2 hours. After quenching with water (20 mL), the mixture was extracted with ethyl acetate (2×20 mL) and the organic phase dried over magnesium sulfate and evaporated under reduced pressure. The residue was chromatographed on silica gel using hexane/ethyl acetate (4:1 and 2:1) to provide the title compound (0.520 g, 60%) as a white solid. $^1$H NMR (CDCl$_3$, 300 MHz) δ: 8.03 (d, J=9.0 Hz, 1H), 7.86–7.83 (A2 of A2B2 system, 2H), 7.75–7.72 (B2 of A2B2 system and A2' of A2'B2' system, 4H), 7.58 (s, 1H), 7.51 (d, J=2.4 Hz, 1H), 7.26–7.21 (B2' of A2'B2' system, 2H), 7.20 (dd, J=2.4 and 9.0 Hz, 1H), 3.97 (t, J=7.3 Hz, 2H), 3.05 (t, J–7.3 Hz, 2H), 2.36 (s, 3H).

EXAMPLE 12

3-(2-Aminoethyl)-5-(2-thienyl)-1H-indole 3-(2-Phthalimidoethyl)-1-(p-toluenesulfonyl)-5-(trifluoromethanesulfonyloxy)-1H-indole (Example 11) (71 mg, 0.12 mmol) was dissolved in 1,2-dimethoxymethane (10 mL). Tetrakis(triphenylphosphine) palladium (14 mg, 0.012 mmol) and lithium chloride (10 mg, 0.24 mmol) were added and the resulting solution was stirred under argon at room temperature for 20 minutes. Thiophene-2-boronic acid (20 mg, 0.15 mmol) and sodium carbonate (2M solution in water, 0.1 ml) were added and the resulting mixture was stirred under argon at reflux for 4 hours. After cooling to room temperature, the crude product mixture was poured into ethyl acetate (20 mL), washed with water (20 mL), dried over magnesium sulfate and evaporated under reduced pressure. The residue was chromatographed on silica gel using hexane/ethyl acetate (4:1) as eluent to provide 3-(2-phthalimidoethyl)-1-(p-toluenesulfonyl)-5-(2-thienyl)-1H-indole (62 mg, 96%) as a colorless oil. $^1$H NMR (CDCl$_3$, 300 MHz) δ:_7.95 (d, J=8.9 Hz, 1H), 7.85–7.82 (A2 of A2B2 system, 2H), 7.80 (d, J=1.4 Hz, 1H), 7.73 (d, J=8.9 Hz, 2H), 7.72–7.69 (B2 of A2B2 system, 2H), 7.55 (dd, J=1.5 and 8.7 Hz, 1H), 7.46 (s, 1H), 7.29 (dd, J=1.2 and 3.5 Hz, 1H), 7.25 (dd, J=1.2 and 5.0 Hz, 1H), 7.19 (d, J=8.9 Hz, 2H), 7.07 (dd, J=3.5 and 5.0 Hz, 1H), 4.00 (t, J=7.4 Hz, 2H), 3.09 (t, J=7.4 Hz, 2H), 2.33 (s, 3H).

To a solution of the above compound (62 mg, 0.12 mmol) in methanol (5 mL) was added hydrazine hydrate (0.1 ml) and the resulting mixture was stirred at room temperature overnight. The solvent was evaporated under reduced pressure and the residue chromatographed on silica gel using hexane/ethyl acetate (2:1) as eluent to provide 3-(2-aminoethyl)-5-(2-thienyl)-1H-indole (15 mg, 53%) as amorphous solid. $^1$H NMR (CD$_3$OD) δ: 10.30 (s, 1H), 7.74 (s, 1H), 7.45–7.35 (m, 2H), 7.25 (d, J=3.8 Hz, 1H), 7.20 (d, J=5.0 Hz, 1H), 7.16 (s, 1H), 7.03 (dd, J=3.8 and 5.0 Hz, 1H).

EXAMPLE 13

Comparison of Binding Affinities

Compounds of the previous examples, as well as reference compounds, were evaluated for binding affinity using cell types receptive specifically to 5-HT$_{1D\alpha}$ and 5-HT$_{1D\beta}$ ligands. The assay protocol generally entailed the incubation of membranes prepared from cells expressing the 1Dβ or 1Dα sub-type of 5-HT receptors, with $^3$H-5-HT. The test compound was incubated at 100 nm concentration with the radioligand and the membrane homogenates prepared from the recombinant cells. After a 60 minute incubation at 22° C., the incubation was terminated by vacuum filtration. The filters were washed with buffer and counted for radioactivity using liquid scintillation spectrometry. The affinity of the test compound for the 5-HT$_{1D\beta}$ or 5-HT$_{1D\alpha}$ receptor estimated by its inhibition of binding of the radioligand to the receptor. The result is expressed desciptively as percent inhibition of binding. Each value is the mean of triplicate determinations. For comparison, sumatriptan was also evaluated. The results are presented in Table 2 below, with reference to the compound numbers of Table 1 and the specific synthesis examples given above.

TABLE 2

| Compound Number | Synthesis Example Number | 5-HT$_{1D\alpha}$ (% Inhibition @ 100 nm) | 5-HT$_{1D\beta}$ (% Inhibition @ 100 nm) |
|---|---|---|---|
| 1 | 8b | 98 | 84 |
| 2 | 8a | 99 | 83 |
| 3 | 2c | 98 | 78 |
| 4 | 2b | 97 | 72 |
| 5 | 4b | 96 | 77 |
| 6 | 8c | 96 | 47 |
| 7 | 12 | 98 | 78 |
| 8 | 7a | 95 | 68 |
| 9 | 2d | 97 | 83 |
| 10 | 2e | 93 | 42 |
| 11 | 2a | 84 | 14 |
| 12 | 4a | 87 | 52 |
| Sumatriptan | — | 95 | 63 |

EXAMPLE 14

Agonist Assay

The in vitro evaluation of the 5-HT$_{1D}$ receptor agonist activity of the compounds of the invention was carried out by testing the extent to which they mimic sumatriptan in contracting the rabbit saphenous vein (Perez, M. et.al. J. Med. Chem. 1995, 38:3602–3607).

Tissues were obtained from male New Zealand White rabbits (c. 3–4 kg) which were sacrificed by an overdose of pentobarbitol. The saphenous veins from both the left and right side were cleaned of fat and connective tissue and placed in Krebs solution (118 mM NaCl, 11 mM glucose, 25 mM NaHCO$_3$, 4,7 mM KCl, 2.5 mM CaCl$_2$2H$_2$O, 1.2 mM KH$_2$PO$_4$ and 1.2 mM MgSO$_4$7H$_2$O). Ring segments of the vein (4–5 mm in length) were cut and the endothelium gently removed. The segments were mounted in 10 mL baths containing Krebs buffer and were constantly aerated with 95% oxygen/5% carbon dioxide and maintained at 37° C. and pH 7.4 in order to record the isometric tension. A resting tension of 2.5 g was applied and the tissues allowed to equilibrate for 90 minutes, with washing every 15–20 minutes. After the equilibrium period, the rings were depolarized by addition of two aliquots of KCl (80 mM final concentration) separated by a 20 minute washing period. The tissues were then exposed to prazosin, idazoxan and indomethacin (all 1 μM in final concentration) for 30 minutes in order to exclude the actions of α$_1$- and α$_2$-adrenergic receptors and prostaglandin receptors respectively. Cumulative concentration-effect curves were then constructed for sumatriptan and the test compounds. Responses were calculated as a percentage of the maximal contraction evoked by 80 mM KCl. Only one compound was tested per preparation.

The following Table 3 illustrates the in vitro activities for the compounds of the invention on the rabbit isolated saphenous vein. EC$_{50}$ represents the concentration of the compound which causes 50% of the maximum contraction effected by it. If the compound induced a maximum contraction of less than 60% of that of KCl (80 mM), it was considered a partial agonist.

TABLE 3

| Example # | EC$_{50}$ (nm) |
|---|---|
| sumatriptan | 220 |
| 8b | 121 |
| 8a | 140 |
| 2c | 432 |
| 2b | 806 |
| 8c | 873 |
| 12 | 607 |
| 7a | 1734 |
| 2e | 888 |
| 2a | 2340 (partial agonist) |

What is claimed is:

1. 5-thiophene-substituted tryptamine analogs exhibiting selectivity towards human 5-HT$_{1D}$ receptors, and corresponding to the general formula I:

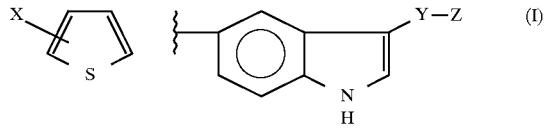

wherein X represents H, C$_1$–C$_4$ alkyl, C$_1$–C$_4$ hydroxyalkyl or halogen, at the 4- or 5-position of the thiophene nucleus, Y represents a direct bond or C$_1$–C$_3$ alkylene group optionally substituted with hydroxyl, and Z represents amino, mono- or di-N-lower alkyl-substituted amino, or optionally N-lower alkyl-substituted pyrrolidine.

2. Thiophene-tryptamine analogs compounds of formula I as claimed in claim 1 in which the thiophene group is unsubstituted, or substituted by a group selected from hydroxymethyl, methyl and chloro.

3. Thiophene-tryptamine analogs of formula I as claimed in claim 1 wherein the thiophene ring is substituted by a substituent group at the 5-position thereof, the substituent being selected from hydroxymethyl, methyl and chloro, with the thiophene nucleus being bonded via its 2-position to the tryptamine nucleus.

4. Thiophene-tryptamine analogs of formula I as claimed in claim 1 in which Z represents a pyrrolidine group, and group Y is a direct bond or methylene.

5. Thiophene-tryptamine analogs according to claim 4 wherein the pyrrolidine group is bonded to group Y through the N-group of the pyrrolidine ring.

6. Thiophene-tryptamine analogs according to claim 4 wherein the pyrrolidine group is bonded to group Y through a carbon atom of the pyrrolidine ring.

7. Thiophene-tryptamine analogs according to claim 6 wherein the N-group of the pyrrolidine ring is substituted with lower alkyl.

8. Thiophene-tryptamine analogs according to claim 7 wherein the substituent on the N-group of the pyrrolidine ring is methyl.

9. Thiophene-tryptamine analogs according to claim 1 wherein Z in the general formula I is amino or mono- or di-N-lower alkyl-substituted amino, and Y is an ethylene group.

10. Thiophene-tryptamine analogs according to claim 9 wherein Z is N-methyl- or N,N-dimethyl-substituted amino.

11. A compound according to claim 1 which is 3-(N-methylpyrrolidin-2R-ylmethyl)-5-(2-thienyl)-1H-indole.

12. A compound according to claim 1 which is 3-(N-methylpyrrolidin-2R-ylmethyl-5-(3-thienyl)-1H-indole.

13. A compound according to claim 1 which is 3-(2-N,N-dimethylaminoethyl)-5-(3-thienyl)-1H-indole.

14. A compound according to claim 1 which is 3-(2-N,N-dimethylaminoethyl)-5-(2-thienyl)-1H-indole.

15. A compound according to claim 1 which is 3-(2-N,N-dimethylaminoethyl-5-(5-hydroxymethyl thienyl-2-yl)-1H indole.

16. A compound according to claim 1 which is 3-(N-methylpyrrolidin-2S-ylmethyl-5-(2-thienyl)-1H-indole.

17. A compound according to claim 1 which is 3-(2-aminoethyl)-5-(2-thienyl)1H-indole.

18. A compound according to claim 1 which is 3-(N-methylpyrrolidin-3-yl)-5-(2-thienyl)-1H-indole.

19. A compound according to claim 1 which is 5-(5-chlorothien-2-yl)-3-(2-N,N-dimethylaminoethyl)-1H-indole.

20. A compound according to claim 1 which is (±)-3-(2-N,N-dimethylamino-1-hydroxylethyl)-5-(3-thienyl)-1H-indole.

21. A compound according to claim 1 which is 3-(2-pyrrolidinylethyl)-5-(2-thienyl)-1H-indole.

22. A compound according to claim 1 which is 3-(2-N,N-dimethylaminoethyl)-5-(5-methylthien-2-yl)-1H-indole.

23. A compound according to claim 1 which is 3-(N-methylpyrrolidin-3-yl)-5-(3-thienyl)-1H-indole.

* * * * *